United States Patent [19]

Uchikubo

[11] Patent Number: 4,882,623
[45] Date of Patent: Nov. 21, 1989

[54] SIGNAL PROCESSING APPARATUS FOR ENDOSCOPE CAPABLE OF CHANGING OUTLINE ENHANCEMENT FREQUENCY

[75] Inventor: Akinobu Uchikubo, Hachioji, Japan

[73] Assignee: Olympus Optical Co., Ltd., Tokyo, Japan

[21] Appl. No.: 230,816

[22] Filed: Aug. 11, 1988

[51] Int. Cl.⁴ .......................... A61B 1/04; H04N 7/18
[52] U.S. Cl. ........................................ 358/98; 358/37; 128/6
[58] Field of Search .................. 358/98, 28, 37; 128/6

[56] References Cited

U.S. PATENT DOCUMENTS 4,766,489  8/1988  Kato ........................................ 358/98

FOREIGN PATENT DOCUMENTS

0136174  7/1985  Japan .
136714  6/1986  Japan .

Primary Examiner—James J. Groody
Assistant Examiner—Victor R. Kostak
Attorney, Agent, or Firm—Armstrong, Nikaido, Marmelstein, Kubovcik & Murray

[57] ABSTRACT

A signal processor for processing signals obtained from an electronic endoscope having an image pickup device which performs photoelectric conversion, the processor having an outline enhancing circuit capable of enhancing outlines within one of a plurality of enhancement frequency ranges, and a circuit capable of selecting one these enhancement frequency ranges. Frequencies that define the range of outline enhancement are thereby varied depending upon the type of the object.

18 Claims, 9 Drawing Sheets

FIG.1

FIG. 3a INPUT SIG. a

FIG. 3b OUTPUT SIG. c FROM 1ST DELAY LINE 31

FIG. 3c OUTPUT SIG. c FROM 2ND DELAY LINE 32

FIG. 3d OUTPUT SIG. d FROM ADDER 33

FIG. 3e OUTPUT SIG. e FROM 1/2 INV.

FIG. 3f OUTLINE ENH. COMP. f

FIG. 3g OUTLINE ENHANCED SIG. g

SIGNAL PROCESSING APPARATUS FOR ENDOSCOPE CAPABLE OF CHANGING OUTLINE ENHANCEMENT FREQUENCY

BACKGROUND OF THE INVENTION

1. Field of the Invention and Related Art Statement

This invention relates to a signal processor which processes signals obtained from an endoscope and which is capable of changing and optimizing outline enhancement frequencies for enhancement of an image outline of an object depending upon the type of the object.

In recent years, endoscopes are increasingly used with an elongated insertion portion capable of being inserted into a body cavity in order to diagnose a symptom of an affected part therein without dissecting any body part and to perform, if necessary, a treatment using desired instruments.

In a system which makes use of a type of endoscope using an image guide, it is difficult to record or reproduce an image obtained by the endoscope. Therefore, endoscopes designed to produce video signals in order to facilitate recording and reproduction of images have been proposed. The following are two types of devices for generating of video signals from an endoscope:

(a) an electronic endoscope which has a solid-state image pickup device disposed in its head portion, wherein video signals are formed from outputs from the image pickup device; and (b) an external endoscope camera which is detachably attached to an ocular portion of a fiber scope for observation which is formed of a bundle of fibers extending from the head to an ocular section of the endoscope, wherein video signals are formed from signals output from the camera.

Outline enhancement can be effected by these systems in such a manner that, as disclosed in Japanese patent application No. 181630/1986, video signals including R (red), G (green) and B (blue) signals and luminance signals are formed from signals obtained by image pickup from an object; and outline enhancement processing is performed with respect to each image signal in the same frequency range predetermined and set in the circuit. The frequency range that defines the range of enhancement cannot be changed.

Examples of objects which can be observed by an endoscope and which need to be observed specially in detail are various lesion portions, vessels, and so forth. The frequency range in which image signals are formed for the image of such a portion covers several MHz.

Accordingly, frequencies which characterize and observed portion differ depending upon the type of the portion, and it is not always possible to obtain optimum outline enhancement effects and, hence, suitable diagnostic performance for an observed portion if a system for observation is used in which the setting of the enhancement frequency range is constant and cannot be changed.

SUMMARY OF THE INVENTION

It is therefore an object of the present invention to provide a signal processor for processing signals obtained from an endoscope, wherein the signal processor is capable of enhancing an outline of a particular portion of an object.

It is another object of the present invention to provide a signal processor for processing signals obtained from an endoscope, wherein the signal processor has a simple construction and is capable of generating image video signals suitable for diagnosis from information supplied from an endoscope.

In accordance with the present invention, an outline enhancement means capable of modifying a signal output from a solid-state image pickup device with respect to frequencies relating to a desired outline enhancement and a means for selecting and setting the outline enhancement frequencies are provided. It is thereby possible for the user to set outline enhancement frequencies suitable for making the contour of a particular observed portion definite.

BRIEF DESCRIPTION OF THE DRAWINGS

FIGS. 1 to 7 relate to a first embodiment of the present invention;

DESCRIPTION OF THE PREFERRED EMBODIMENTS

Figure 1:
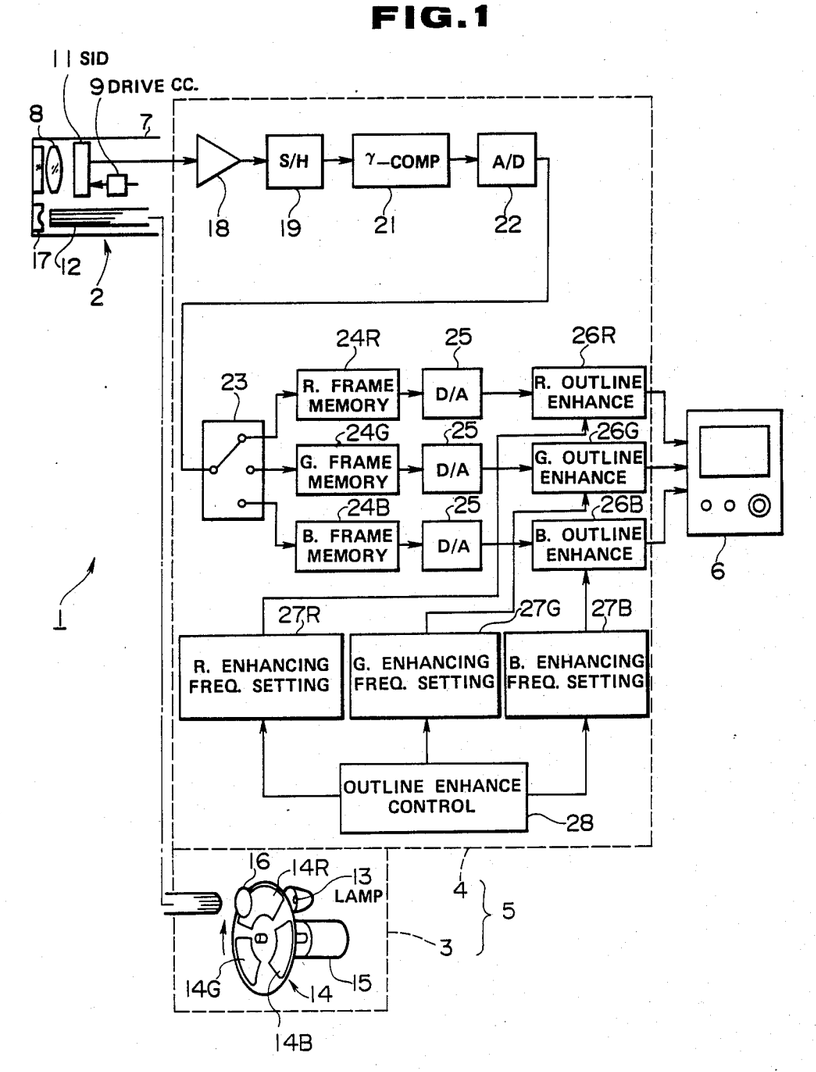
FIG. 1 is a diagram of the construction of an endoscope apparatus which includes the first embodiment.

Referring to FIG. 1, an endoscope apparatus 1 which includes a first embodiment of the present invention is has an elongated electronic endoscope 2 for insertion into a body cavity; an endoscope video processor 5 to which the electronic endoscope 2 can be connected and which has a light source 3 and a signal processing section 4; and a display unit 6 such as a CRT monitor for displaying video signals output from the signal processing section 4 of the endoscope video processor 5.

In the electronic endoscope 2, an imaging objective 8 is accommodated in an elongated insertion portion 7 at the head thereof, and a solid-state image pickup device (hereinafter referred to as "SID") which is driven by a drive circuit 9 is disposed on the focal plane of the objective 8.

A light guide 12 which is provided as an illumination light transmitting means and which is formed of a flexible fiber bundle extends through the insertion portion 7. A rear end of the light guide 12 can be detachably attached to the light source 3. A light source lamp 13 is disposed in the light source 3, and a rotary color filter assembly 4 is disposed in front of the light source lamp 13. The rotary color filter assembly 4 is constructed in such a manner that color-transmission filters 14R, 14G, and 14B of three primary colors: red, green, and blue are attached to sectoral apertures arranged in the peripheral direction. The rotary filter assembly 14 is driven by a stepping motor 15. Lights having wavelengths in correspondence with red, green, and blue are successively obtained from white light emitted from the light source lamp 13 by the color-transmission filters 14R, 14G, and 14B while these filters are successively placed in the illumination optical path. These lights are converged by a condenser lens 16 and are introduced into the light guide 12 from the rear end thereof. The illumination light composed of these lights travels through the light guide 12 and is thereafter emitted from the front end of the light guide 12. The illumination light illuminates, through a light distribution lens 17, the object with different colors successively changed.

Reflection lights corresponding to color lights of red, green and blue travel through the objective lens 8 and are successively received by the SID 11. Signals corresponding to respective pixels of the SID 11 are successively outputted, for example, in a lateral direction in response to a clock signal applied from the drive circuit 9 to the SID 11. These pixel signals are amplified by a preamplifier 18, and video signals are extracted from the pixel signals by a sample and hold circuit 19. These video signals are $\gamma$-corrected by a $\gamma$-compensation circuit 21 and are thereafter converted into digital signals by an A/D converter 22. These video signals are changed over by a multiplexer 23 in synchronism with the sequential-color surface illumination and are successively stored in R frame memory 24R, G frame memory 24G and B frame memory 24B which correspond to items of red, green, and blue information, respectively. The frame memories 24R, 24G, and 24B are simultaneously read laterally at a speed matching with the display speed of the display unit or CRT monitor 6, and signals obtained by this reading are converted into analog signals: R, G and B signals by a D/A converter 25.

These R, G, and B signals undergo outline enhancement processing performed by a red outline enhancing circuit 26R, a green outline enhancing circuit 26G, and a blue outline enhancing circuit 26B which constitute essential portions of the first embodiment. Frequency ranges in which these signals are changed by the outline enhancing circuits 26R, 26G, and 26B to enhance an outline are respectively set by a red enhancement frequency setting circuit 27R, a green enhancement frequency setting circuit 27G and a blue enhancement frequency setting circuit 27B. The R, G and B signals are thereby processed for outline enhancement with respect to the same desired frequency range.

The setting (selection) of the frequency range with which outline enhancement is effected is controlled by an outline enhancement control circuit 28. A command signal is supplied to the outline enhancement control circuit 28 by a simple operation of a switch or the like, and the frequency range in which outline enhancement is effected is controlled on the basis of this command signal. After the R, G, and B signals have been processed for outline enhancement by the outline enhancing circuits 26R, 26G, and 26B, they are inputted into the display unit or CRT monitor 6 so that the image of the object is displayed in the display frame in colors.

The constitution of each of the outline enhancing circuits 26R, 26G, and 26B will be described below.

The outline enhancing circuits 26R, 26G, and 26B have the same construction and one of them is therefore representative of the others and will be indicated by a reference character 26.

Figure 2:
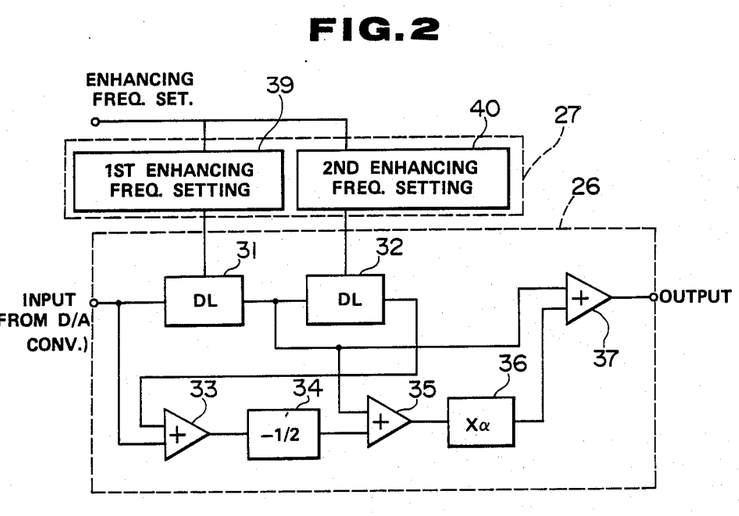
FIG. 2 is a diagram of a horizontal outline enhancement circuit.

As shown in FIG. 2, the outline enhancing circuit 26 is constituted by a first delay line 31 for delaying an input signal, a second delay line 32 for further delaying a signal output from the first delay line 31, an adder 33 which adds an input signal and a signal output from the second delay line 32 to each other, a ½ inverter 34 which inverts a signal output from the adder 33 after the level of this signal has been reduced by half, an adder 35 which adds a signal output from the ½ inverter 34 and the signal output from the first delay line 31 to each other, a multiplier 36 which multiplies a signal output from the adder 35 so as to set this signal to a predetermined level, and an adder 37 which adds a signal output from the multiplier 36 and the signal output from the first delay line 31 to each other and outputs the result of this addition. The lengths of time of delay effected by the delay lines 31 and 32 are changed by first and second enhancement frequency setting circuits 39 and 40 which constitute the enhancement frequency range setting circuit (27, representative of the others). The enhancement frequency range can be varied in response to the change in the delay time.

The opertion of the outline enhancing circuit 26 will now be described with reference to FIGS. 3.

Figure 3A:
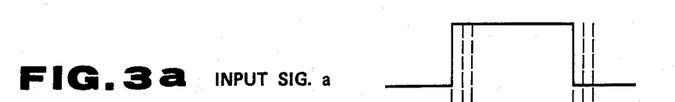
FIGS. 3 are diagrams of the operation of the circuit shown in FIG. 2.
Figure 3B:
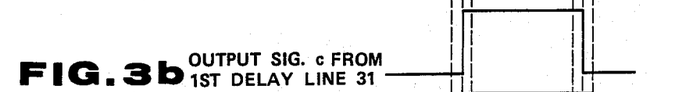
Figure 3C:
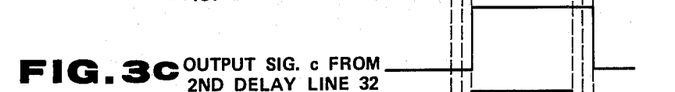
Figure 3D:
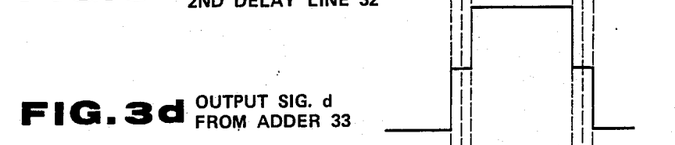
Figure 3E:
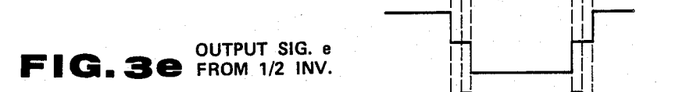
Figure 3F:
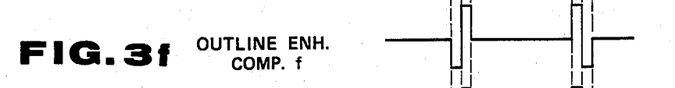
Figure 3G:
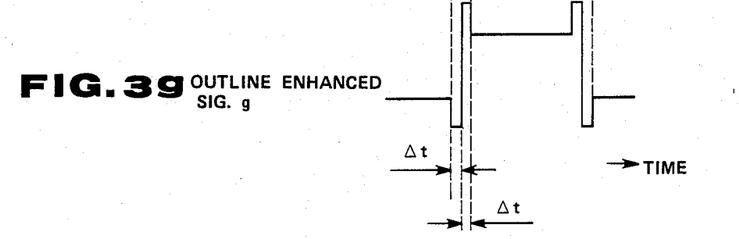

An input signal such as the one indicated in FIG. 3a is delayed by $\Delta t$ and $2\Delta t$ as it passes through the first and second delay lines 31 and 32, as indicated in FIGS. 3b and 3c. The signal a and a signal c which is outputted from the second delay line 32 after it has been delayed twice as much as an output signal b shown in FIG. 3b are added to each other by the adder 33 in order to form an output signal d as shown in FIG. 3d. The level of the signal d output from the adder 33 is reduced by half by the ½ inverter 34 and is inverted to form an output signal e as shown in FIG. 3e. The output signal e and the signal b output from the first delay line 31 are added to each other by the adder 35, thereby obtaining an outline enhancing component f as shown in FIG. 3f. This outline enhancing component is set to a predetermined level by the multiplier 36, and this multiplied signal and the signal b output from the first delay line 31 are added to each other by the adder 37, thereby obtaining an output signal g in accordance with the desired outline enhancement, as shown in FIG. 3g.

If the time of delay effected by each of the delay lines 31 and 32 is set to several hundred ns, the outline enhancing circuit 26 serves as a horizontal outline enhancement circuit for performing outline enhancement in the horizontal direction. If the delay time is set to a value corresponding to one horizontal scanning line by employing a 1-H delay line or the like which is generally used, the outline enhancing circuit 26 serves as a vertical outline enhancement circuit for performing outline enhancement in the vertical direction. In accordance with this embodiment, the outline enhancing circuit 26 is designed to be formed of horizontal and vertical outline enhancement circuits which are connected in series no matter which one is disposed in front of the other.

Figure 4:
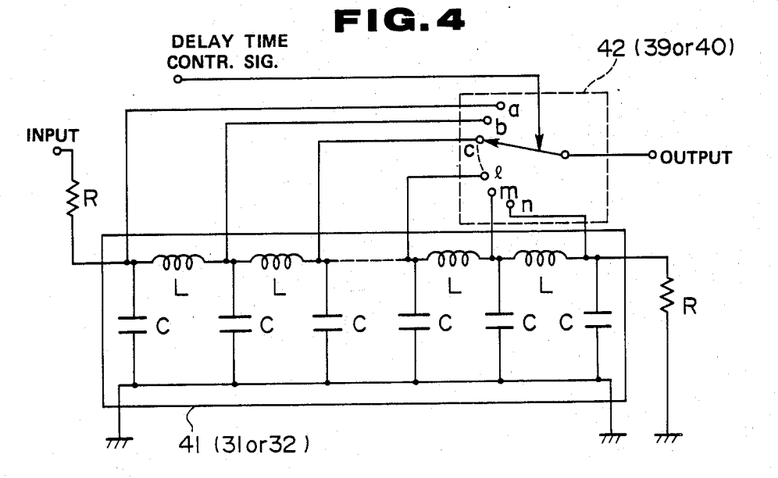
FIG. 4 is a circuit diagram of an example of an enhancement frequency setting circuit.

The constitution of an essential section of a type of enhancement frequency range setting circuit will be described below with reference to FIG. 4. (Portions shown in FIG. 4 correspond to those indicated by 31 and 39 or 32 and 40 in FIG. 2.)

A signal which is to be modified for outline enhancement is applied to the input terminal of a tapping-type delay line 41 via a matching resistor R. The tapping-type delay line 41 is formed in such a manner that coils L which are connected to each other in series are interposed between the output and input terminals while connections between the coils L as well as the input and output terminals are respectively grounded via capacitors C.

The output terminal is also grounded via a matching resistor R. Taps are extended from the connections between the coils and the capacitors C and are connected to contacts a, b, ... n of an analog switch 42. Delay signals are outputted from a common contact of the analog switch 42. In the analog switch 42, one of the contacts to be electrically connected to the common contact is selected by a delay time control signal (corresponding to the outline frequency range setting input shown in FIG. 2). If the common contact is connected to, for example, the contact b, the delay time is set to a minimum unit value. The delay time gradually increases as the common contact is shifted over the contacts c, l, m, and n.

Figure 5:
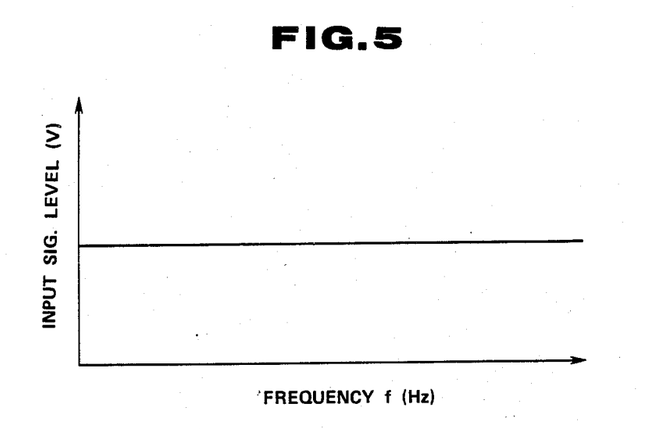
FIG. 5 is a graph of an example of the frequency characteristics of a signal input into an outline enhancing circuit.
Figure 6:
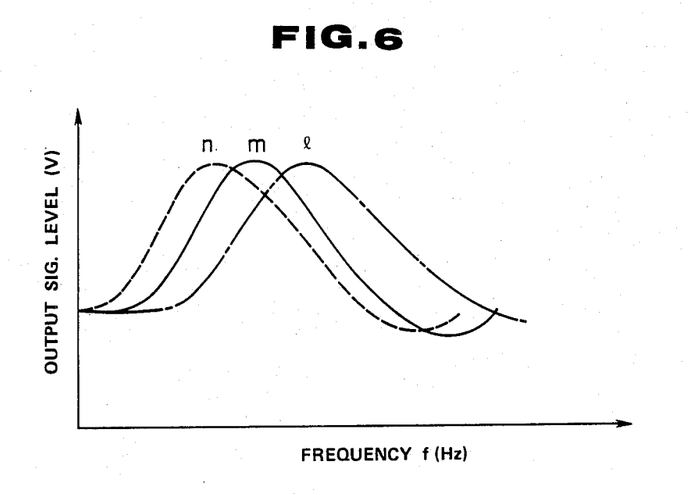
FIG. 6 is a graph of examples of frequency characteristics of an output signal processed for outline enhancement by changing the amount of delay relative to the input signal shown in FIG. 5.

A finer portion of the image are displayed by video signals of higher frequencies. If the delay time is short, the time shift between the waveforms a, b, and c in FIG. 3 is small. This means an enhancement of a change in the signal level during a short time period, namely enhancement of an outline detected at a high frequency. Therefore, if a signal such as the one shown in FIG. 5 which is flat with respect to frequencies is supplied to the circuit shown in FIG. 2 and if the tap is successively changed over via the contacts l, m, and n, the output from the circuit of FIG. 2 changes such that it effects enhancement at a lower frequency, as shown in FIG. 6, as the delay time increases in response to switching to l, m, and n. The circuit may be designed to change or select the outline enhancing level by varying the coefficient used in the multiplier 36 as shown in FIG. 2.

Figure 7:
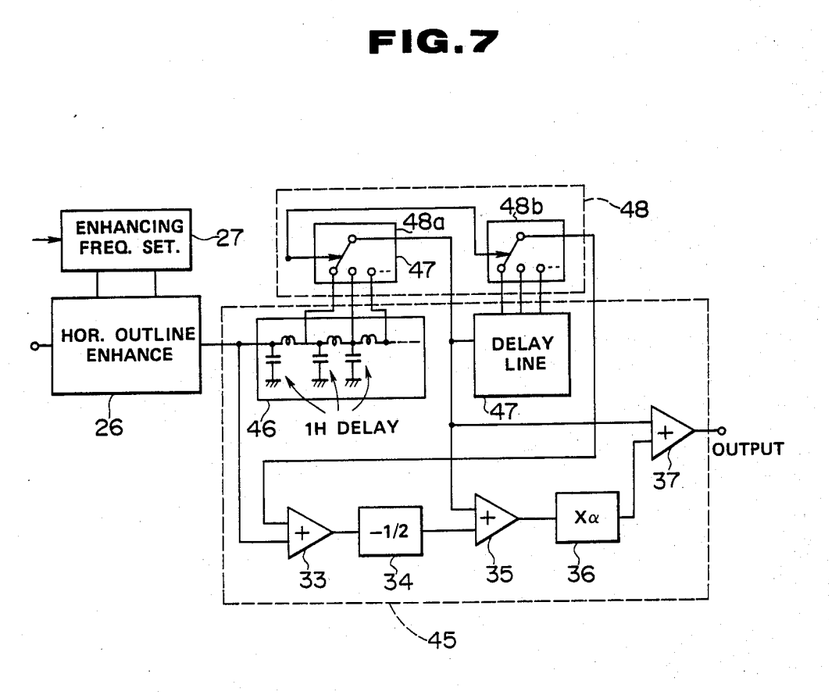
FIG. 7 is a diagram of a vertical outline enhancement circuit.

As shown in FIG. 7, a vertical outline enhancement circuit 45 may be connected in series to the horizontal outline enhancement circuit 26 so as to also enable outline enhancement in the vertical direction.

The vertical outline enhancement circuit 45 has first and second delay lines 46 and 47 which have taps corresponding to lengths of time obtained by multiplying one horizontal term by integers. The amounts of delay effected by these delay lines are substituted for those effected by the first and second delay lines 31 and 32 of the horizontal outline enhancement circuit 26 shown in FIG. 2. The amounts of delay effected by the first and second delay lines 46 and 47 can be selected and set via multiplexer 48a and 48b which constitute an enhancement frequency setting circuit 48, thereby changing and setting the vertical enhancement frequency range. Except for this, the construction is the same as that shown in FIG. 2, and corresponding components are indicated by the same reference characters. This design also makes it possible to freely set the outline enhancement frequency range in the vertical outline enhancement circuit 45. The outline enhancement control circuit 31 can readily be realized by employing a control means such as a microcomputer.

In the above-described embodiment, the frequency range in which an outline enhancement is effected can be freely set, thereby improving in the resolution relating to a particular target portion.

There are various frequency components in video signals which characterize a part of the body if this part has many organic plicae or a cluster of fine vessels. In accordance with the present invention, it is possible to set the enhancement frequencies as desired so as to improve the resolution with respect to various types of parts of the body. Therefore, various lesion portions can readily be diagnosed in an optimized manner. In other words, the frequency range within which outline enhancement is performed is set as desired by a simple operation of a switch or the like, and the outline enhancement is effected in the set frequency range, thus making it possible to enhance, in a suitable manner, an outline of a part of the observed image which should be mainly observed with improved resolution. Consequently, this important portion can be readily diagnosed with improved resolution.

In this embodiment, R, G, and B signals are used to display colors of an image, but these color signals can be replaced with signals for complementary colors: cyan, magenta and yellow. In this embodiment, the outline enhancement circuit is provided for each of R, G, and B signals. However, the outline enhancement circuit may be provided for only one or two of the R, G, and B signals.

Figure 8:
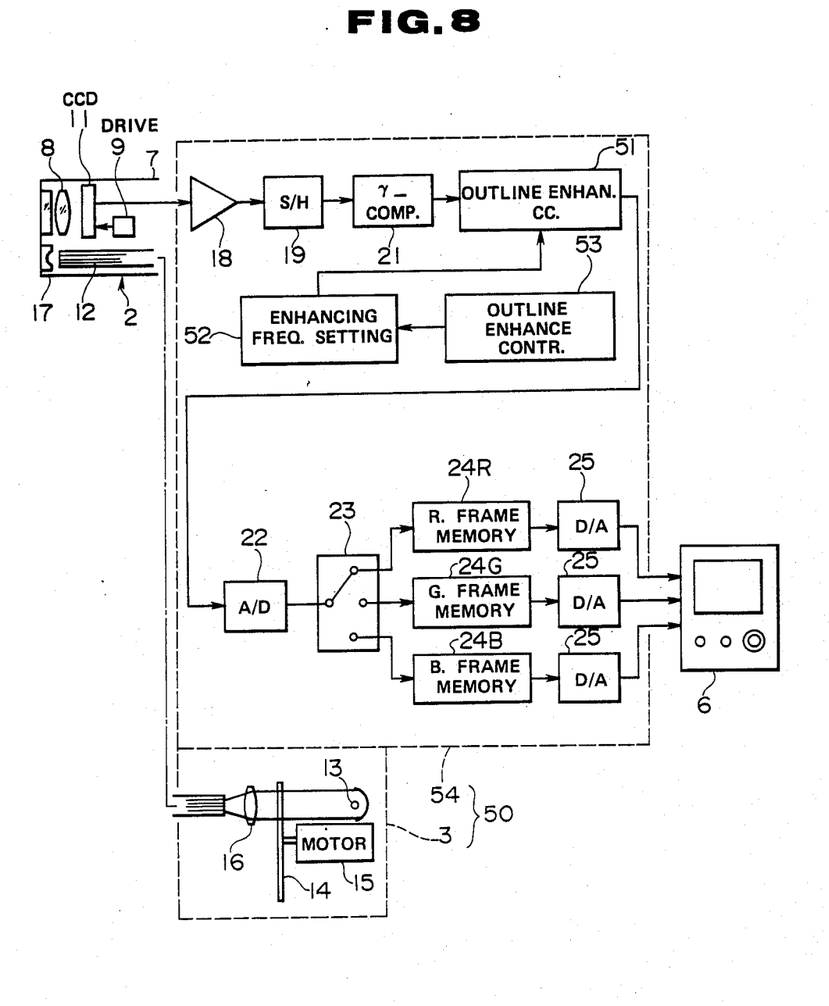
FIG. 8 is a diagram of the construction of a second embodiment of the present invention.

FIG. 8 shows an endoscope apparatus which includes a second embodiment of the present invention.

While the first embodiment is provided with the (endoscope) video processor 5 having the outline enhancement circuits 26R, 26G, and 26B for color signals R, G, and B which have been read from the frame memories 24R, 24G, and 24B and converted into analog values by the D/A converter 25, a video processor of this second embodiment has an outline enhancement circuit 51 and an outline enhancement setting circuit 52 interposed between the γ-compensation circuit 21 and the A/D converter 22. The setting of the degree of outline enhancement and the enhancement frequency range relating to the operation of the outline enhancement circuit 51 is performed by the outline enhancement setting circuit 52, and set values in this setting are controlled by a control signal issued from an outline enhancement control circuit 53. The signal processing section in this embodiment is indicated by a reference character 54.

In this embodiment, R, G, and B signals are successively inputted into the outline enhancement circuit 51, and the enhancement frequency range set by the outline enhancement setting circuit 52 is changed in synchronization with the switching of the R, G, and B signals, thereby modifying R, G, and B signals to effect outline enhancement in the same frequency range.

When, in this circuit arrangement, the setting of the enhancement frequency range is changed, the timing of the outline enhancement signal input into the A/D converter, namely, Δt in FIGS. 3 is also changed. This effect is in common with the vertical outline enhancement and horizontal outline enhancement. In accordance with this embodiment, therefore, it is necessary to delay the input or the output of the outline enhancement circuit in synchronism with the change in the setting of the enhancement frequency range on the basis of the maximum extent of change in the setting so that the output from the outline enhancement matches with the A/D converter before it is inputted therein.

In accordance with this embodiment, it is sufficient to provide only one circuit unit as the outline enhancement circuit 51 as well as the enhancement setting circuit 52. Other functions and effects are the same as the first embodiment. The vertical outline enhancement circuit and the horizontal outline enhancement circuit can be formed no matter which one may be disposed in front of the other. The outline enhancement circuit may be interposed between the sample and hold circuit 19 and the γ-compensation circuit 21.

Figure 9:
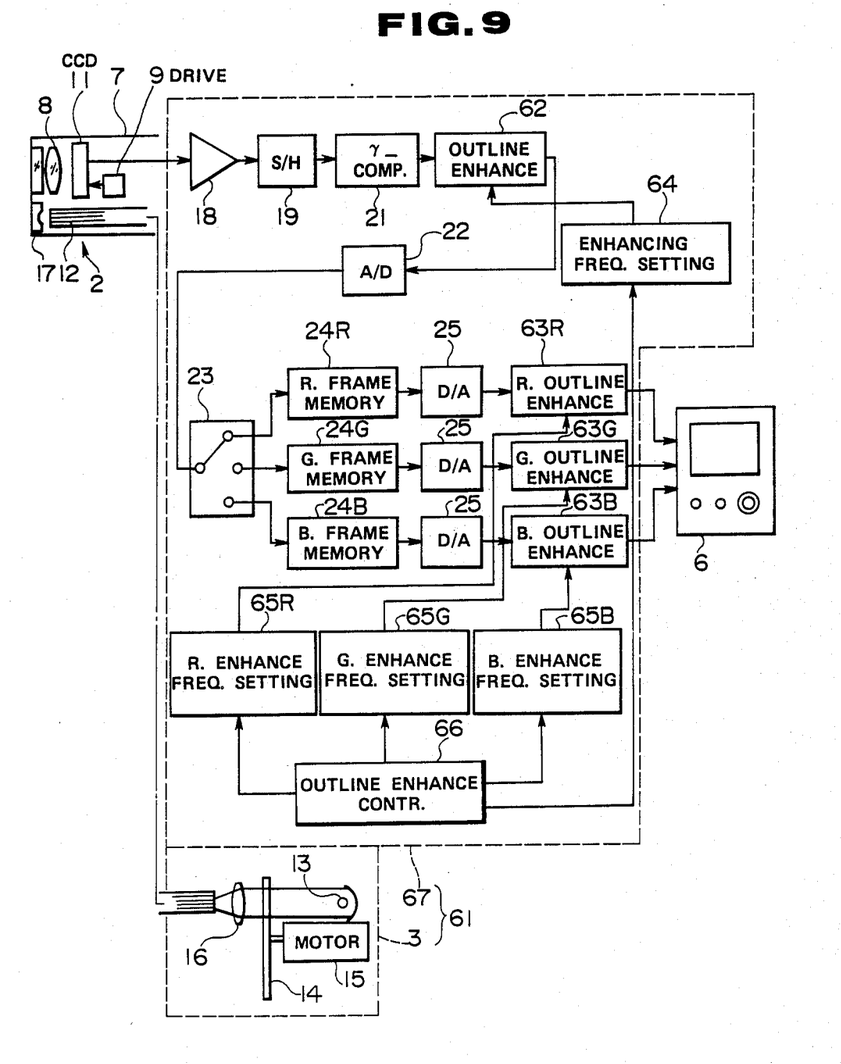
FIG. 9 is a diagram of the construction of a third embodiment of the present invention.

FIG. 9 shows a third embodiment of the present invention.

A video processor 61 employed in this embodiment is constructed in such a manner that one horizontal outline enhancement circuit or a vertical outline enhancement circuit is inserted at a position corresponding to the position of insertion of each outline enhancement circuit in the first and second embodiment. If an outline enhancement circuit 62 is a horizontal outline enhancement circuit, outline enhancement circuits 63R, 63G, and 63B are vertical outline enhancement circuits. Of course, the converse is also possible. The A/D converter 22 must be consistently supplied with signals with the same timing based on the matching effected by delaying the input or output of the outline enhancement circuit 62 in response to changes in the enhancement frequency range, as described above with respect to the second embodiment. The enhancement frequency range relating to the operation of the outline enhancement circuit 62 can be changed by an enhancement frequency setting circuit 64 while the enhancement frequency ranges relating to the operations of the other outline enhancement circuits 63R, 63G, and 63B are changed by enhancement frequency setting circuits 65R, 65G, and 65B which can output control signals representing set values of the desired enhancement frequency ranges under the control of an outline enhancement control circuit 66. The signal processing section in this embodiment is indicated by a reference character 67.

In accordance with this embodiment, only one circuit unit is used as the outline enhancement circuit 62, and it is sufficient to effect matching of the amount of delay with respect to only one line. Therefore, the number of circuit units is smaller than that in the case of the first embodiment. Other functions and effects are the same as the second embodiment.

Figure 10:
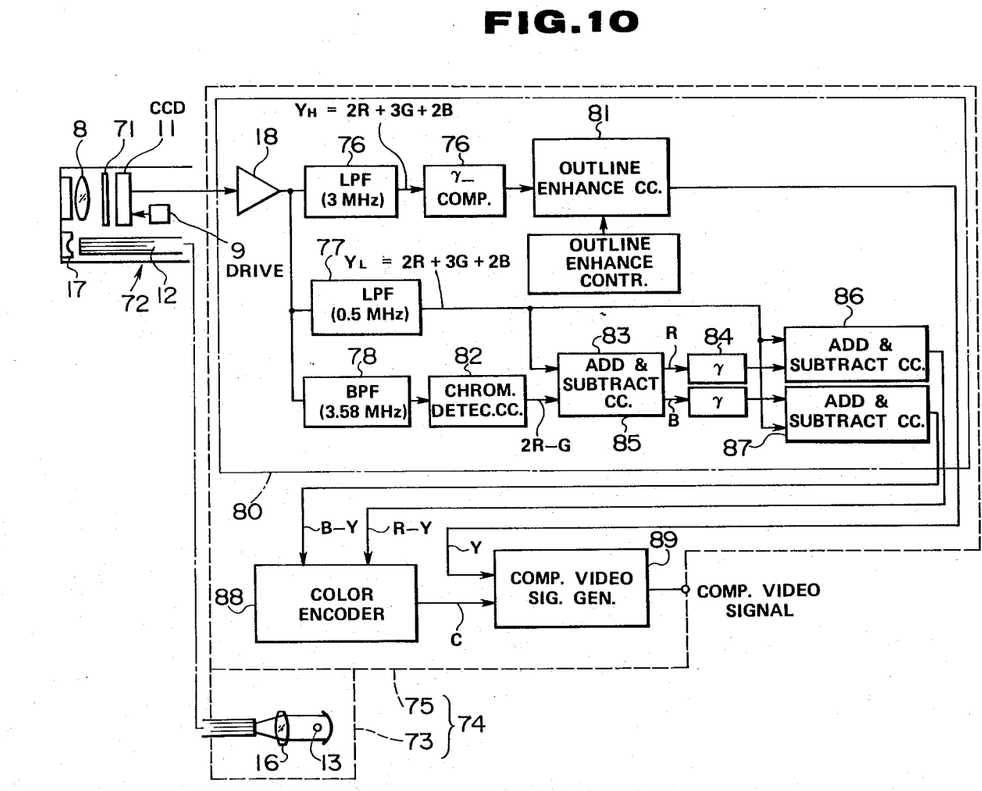
FIG. 10 is a diagram of the construction of a fourth embodiment of the present invention.

FIG. 10 shows a fourth embodiment of the present invention.

This embodiment makes use of a single plate type of electronic endoscope 72 which has a color separation filter 71 disposed in front of the SID 11. A video processor 74 which has the single plate electronic endoscope 72 and a light source 73 are used.

A signal output from the SID 11 is amplified by a preamplifier 18 in a signal processing section 75 and is supplied to low-pass filters 76 and 77 and a band-pass filter 78. The output from the preamplifier 18 is converted into a high-frequency luminance signal $Y_H$ and a low-frequency luminance signal $Y_L$ by the low-pass filters 76 and 77. The composition of each of the high-frequency and low-frequency luminance signals, $Y_H$ and $Y_L$ is 2R+3G+2B.

The luminance signal $Y_H$ is γ-corrected by a γ-compensation circuit 79 and undergoes outline enhancement processing in an outline enhancement circuit 81. This outline enhancement processing is performed in conformity with the first embodiment.

On the other hand, components of the signal output from the preamplifier 18 other than color components thereof are cut by the band-pass filter 78, and the signal output therefrom is supplied to a color demodulator circuit 82. Color components obtained by the band-pass filter 78 are demodulated into 2R-G, 2B-G signals by the color demodulator circuit 82. Outputs 2R-G and 2B-G from the color demodulator circuit 82 and the output from the low-pass filter 77, namely $Y_L$ are converted into R and B signals by an addition/subtraction circuit 83, as shown below:

$Y_L$-(2B-G)+4(2R-G)=2R+3G+2B-2B+G+8R-4G=10R ... ①
$Y_L$-(2R-G)+4(2B-G)=2R+3G+2B-2R+G+8B-4G=10B ... ②

Addition/subtraction circuits 86 and 87 subtract from the luminance signal $Y_L$ R and B signals which have passed through the γ-compensation circuits 84 and 85 so that they generate color-difference signals R-Y and B-Y. The luminance/color-difference signal generating section is indicated by a reference character 80. The color-difference signals R-Y and B-Y are converted into a chroma signal C by a color encoder circuit 88 which is combined with the luminance signal, $Y_H$ and is converted into a composite video signal.

The light source 73 introduces white light of the lamp 13 to the incidence end surface of the light guide 12 via the condenser lens 16, thereby illuminating the object with white light.

In this embodiment, outline enhancement is effected with respect to the luminance signal $Y_H$ alone. However, the luminance signal $Y_L$ and the color signals R and B may be respectively modified for outline enhancement.

Figure 11:
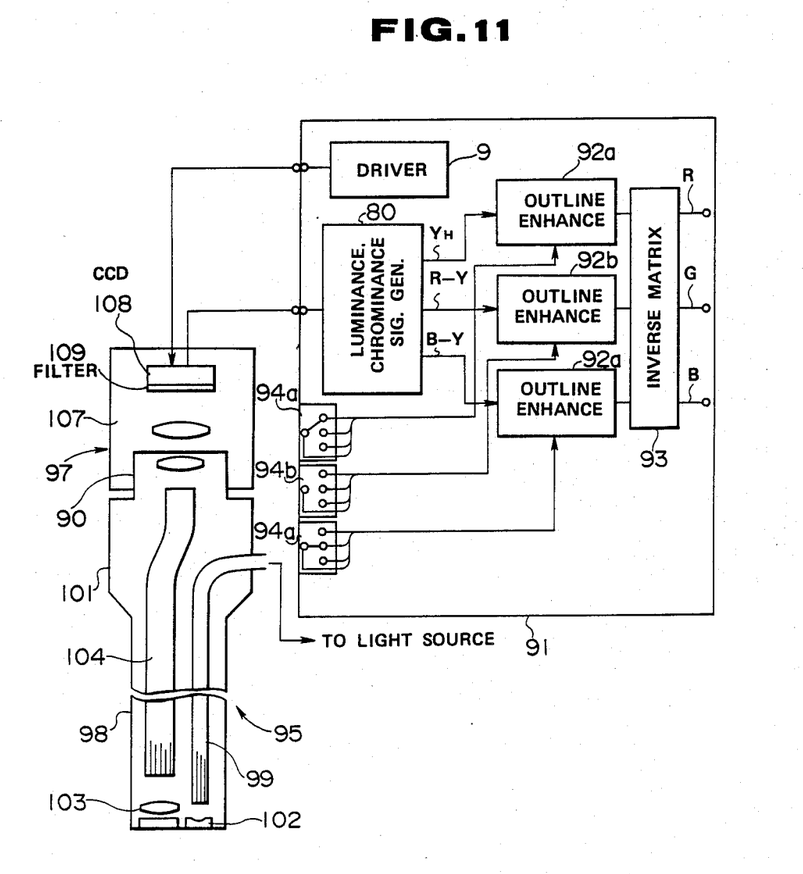
FIG. 11 is a diagram of the construction of a fifth embodiment of the present invention.

FIG. 11 shows a fifth embodiment of the present invention in which outline enhancement can be effected with respect to each of the luminance signal $Y_H$, the color-difference signals R-Y and B-Y independently. That is, in a signal processing section 91 of this embodiment, the luminance signal $Y_H$ and the color-difference signals R-Y and B-Y are respectively supplied to outline enhancement circuits 92a, 92b and 92c and are supplied to an inverse matrix circuit 93, thereby generating three primary color signals, R, G, and B which are outputted to a color monitor.

Each of the outline enhancement circuits 92a, 92b, and 92c is constituted by, for example, the horizontal and vertical outline enhancement circuits 26 and 25 shown in FIG. 7, and enhancement frequencies are independently selected and set by selection switches 94a 94b and 94c. In this embodiment, the drive circuit 9 is disposed in the signal processing section 91.

In this embodiment, a fiber scope 95 and an external TV camera 97 capable of being attached to an ocular portion 96 of the fiber scope 95 provide for a different type of electronic endoscope.

The fiber scope 95 is constructed in such a manner that a light guide 99 is inserted into and extended through an elongated insertion portion 98, and an incidence end portion of the light guide 99 extends to the outside of an operational portion 101 so that it can be attached to a light source. Illumination light supplied therefrom to the incidence end surface is transmitted to an emergence end surface and is emitted to an object via a light distribution lens 102. An ocular lens 103 is disposed in a head portion of the insertion portion 98 so that an image of the object is formed at the incidence end surface of an image guide 104. This optical image is transmitted through the image guide 104 to the emergence end surface thereof and is made to pass through an ocular lens 105 so that it can be osberved by the naked eye. If the TV camera 97 is attached to the ocular portion 96, the transmitted optical image is imaged on a CCD 108 by an imaging lens 107. A mosaic color filter 109 is attached to the image pickup surface of the CCD 108, thereby effecting color separation into red, green or blue with respect to, for example, each pixel.

The present invention can also be applied to an external endoscope camera having an image pickup device, for example a three-tube type or a three-plate type of image pickup because it provides, with this type of camera, an outline enhancing performance similar to that in the case of the first to third embodiments.

The image display system in accordance with the present invention is not limited to the color display type. Instead, it may be a black-and-white display type.

The light sources 3 and 73 are not limited to the type suited to be incorporated in the video processors 5 and 61, and a type of light source provided separately from the video processor is also possible.

In the above-described embodiments, only one frequency range is set for enhancement in the horizontal or vertical direction. However, a plurality of outline enhancement circuits in series connection may be provided so that they effect outline enhancement with respect to different frequency ranges. This method enables outline enhancement over the entire area of a portion to be observed in a case where the portion being observed not only has an outline which can be depicted within a single frequency range, but also a configuration which has to be depicted in a plurality of frequency ranges.

Other embodiments of the present invention can be provided on the basis of certain combinations of the above-described embodiments.

What is claimed is:

1. A signal processor for processing signals obtained from an electronic endoscope having an image pickup device, said signal processor, comprising:
    video signal processing means operably connected to said image pickup device for processing an output signal from said image pickup device so as to obtain desired video signals;
    outline enhancing means operably connected to said image pickup device including said video signal processing means for changing a frequency range and for processing an output signal from said image pickup device to thereby effect outline enhancement; and
    means operably connected to said outline enhancing means for selecting and setting said frequency range relating to the operation of said outline enhancing means.

2. A signal processor according to claim 1, wherein said outline enhancing means has a first circuit means for effecting outline enhancement in the horizontal direction.

3. A signal processor according to claim 1, wherein said outline enhancing means has a second circuit means for effecting outline enhancement in the vertical direction.

4. A signal processor according to any one of claims 1 to 3, wherein said outline enhancing means is provided for at least one of a plurality of color signals.

5. A signal processor according to any one of claims 1 to 3, wherein said outline enhancing means is for modifying a luminance signal and a color-difference signal to effect outline enhancement.

6. A signal processor according to any one of claims 1 to 3, wherein said outline enhancing means is for modifying only a luminance signal to effect outline enhancement.

7. A signal processor according to any one of claims 1 to 3, wherein said outline enhancing means has a tapping type of delay line having taps to obtain different amounts of delay.

8. A signal processor according to any one of claims 1 to 3, wherein said selecting and setting means is has a change-over switch which selects one of a plurality of contacts relating to different amounts of delay.

9. An electronic endoscope apparatus, comprising:
    an electronic endoscope having an elongated insertion portion, an illuminating optical means for emitting illuminating light from a head portion of said insertion portion, an imaging objective disposed in the head portion of said insertion portion, and an image pickup device for effecting photoelectric conversion of an image formed by said objective;
    a drive circuit means operably connected to said image pickup device for outputting a drive signal to be read by said image pickup device;
    signal processing means operably connected to said image pickup device for processing a signal output from said image pickup device in response to said drive signal so as to generate a predetermined image signal;
    monitor means operably connected to said signal processing means for displaying an object image on the basis of said predetermined image signal output from said signal processing means;
    light source means for supplying said illuminating optical means with illumination light;
    outline enhancing means including said signal processing means for effecting outline enhancement of the object image displayed on said monitor means in one of a plurality of enhancement frequency ranges; and
    change-over means for changing said plurality of enhancement frequency ranges.

10. An electronic endoscope apparatus according to claim 9, wherein said electronic endoscope further includes an electronic scope wherein said image pickup device is disposed at an imaging position of said objective.

11. An electronic endoscope apparatus according to claim 9, wherein said electronic endoscope having an optical scope with an image guide for transmitting an image formed by said objective, and a TV camera coupled to an ocular portion of said optical scope for incorporating an imaging lens means for forming an optical image transmitted by said image guide and an image pickup device for effecting photoelectric conversion of an image formed by said imaging lens means.

12. An electronic endoscope apparatus according to any one of claims 9 to 11, wherein said outline enhancing means has a horizontal outline enhancement circuit means for effecting outline enhancement in the horizontal direction.

13. An electronic endoscope apparatus according to any one of claims 9 to 11, wherein said outline enhancing means has a vertical outline enhancement circuit means for effecting outline enhancement in the vertical direction.

14. An electronic endoscope apparatus according to claim 12, wherein said outline enhancing means having a tapping type of delay line having taps to obtain different amounts of delay.

15. An electronic endoscope apparatus according to claim 9, wherein said change-over means includes a selection switch which selectively turns on or off one of a plurality of contacts connected to delay means for effecting different amounts of delay.

16. An electronic endoscope apparatus according to claim 15, wherein said selection switch can be changed over manually.

17. An electronic endoscope apparatus according to claim 15, wherein said selection switch can be changed over and controlled by an electrical signal.

18. An electronic endoscope apparatus according to claim 13, wherein said outline enhancing means is constituted by employing a tapping type of delay line having taps to obtain different amounts of delay.

* * * * *